US008992495B1

(12) United States Patent
Howell

(10) Patent No.: US 8,992,495 B1
(45) Date of Patent: Mar. 31, 2015

(54) WRAP-AROUND CANINE UTILITY HARNESS WITH INTEGRAL DIAPER

(75) Inventor: Dawn Marie Howell, Elkhorn, NE (US)

(73) Assignee: Bymoms4pets, LLC, Ames, IA (US)

( * ) Notice: Subject to any disclaimer, the term of this patent is extended or adjusted under 35 U.S.C. 154(b) by 536 days.

(21) Appl. No.: 13/452,285

(22) Filed: Apr. 20, 2012

Related U.S. Application Data

(63) Continuation of application No. 13/342,829, filed on Jan. 3, 2012, now abandoned, and a continuation of application No. 13/342,813, filed on Jan. 3, 2012, now abandoned.

(60) Provisional application No. 61/571,741, filed on Jul. 5, 2011.

(51) Int. Cl.
  *A61F 13/15* (2006.01)
  *A01K 23/00* (2006.01)

(52) U.S. Cl.
  CPC .................................... *A61F 13/15* (2013.01)
  USPC ................. 604/385.09; 604/385.01; 119/868; 119/869

(58) Field of Classification Search
  USPC ........ 604/385.09, 385.01; 119/868, 867, 869, 119/863, 856
  See application file for complete search history.

(56) References Cited

U.S. PATENT DOCUMENTS

| 4,813,949 | A |  | 3/1989 | O'Rourke |
| 5,226,386 | A | * | 7/1993 | Thoma ......................... 119/869 |
| 5,555,847 | A |  | 9/1996 | Kelly |
| 6,142,405 | A | * | 11/2000 | Black .......................... 242/388.6 |
| 6,368,313 | B1 | * | 4/2002 | Howard .................... 604/385.09 |
| 6,895,901 | B1 | * | 5/2005 | Howard ....................... 119/869 |
| 7,464,668 | B2 |  | 12/2008 | Brewington |
| 7,753,008 | B2 |  | 7/2010 | Krenkel |
| 8,302,565 | B2 | * | 11/2012 | Williams ...................... 119/868 |
| 2004/0074450 | A1 |  | 4/2004 | Soares et al. |
| 2006/0196447 | A1 | * | 9/2006 | Poh-Beyerlein et al. ..... 119/869 |

* cited by examiner

*Primary Examiner* — Jacqueline F. Stephens
(74) *Attorney, Agent, or Firm* — Suiter Swantz pc llo

(57) ABSTRACT

Wrap-around canine utility harness with integral diaper comprises a body wrap utility harness apparatus with a detachable integral diaper. The harness apparatus may secure the integral diaper covering the anus and urethra while still maintaining utility and protection as a dog control harness. The harness apparatus is comprised of a fabric wrap in two perpendicularly connected sections. A longitudinal wrap forms a continuous cover from a withers area caudally along the dorsal, wrapping around the posterior of the dog, cranially over the ventral ending near the upper chest. A perpendicularly attached trunk wrap section completely encircles trunk of the dog overlapping and attaching at the dorsal. The integral diaper extends from above the tail encircling the base of the tail, around the rump to a caudal-cranial midpoint on the ventral able to contain excrement and protect anus and urethra area for both male and female dogs.

16 Claims, 7 Drawing Sheets

WRAP-AROUND CANINE UTILITY HARNESS WITH INTEGRAL DIAPER

CROSS-REFERENCE TO RELATED APPLICATIONS

The present application is a continuation of and claims priority to U.S. Non-Provisional application Ser. No. 13,342,829 filed Jan. 3, 2012 now abandoned and is also a continuation of and claims priority to U.S. Non-Provisional application Ser. No. 13,342,813 filed Jan. 3, 2012, now abandoned both of which claim the benefit under 35 U.S.C. §119(e) of U.S. Provisional Application Ser. No. 61/571,741, filed Jul. 5, 2011, all of which are incorporated herein by reference in their entirety.

TECHNICAL FIELD

The present disclosure generally relates to the field of pet harnesses, and more particularly to a versatile pet utility harness and integrated diaper useful for containing canine excrement.

BACKGROUND

An owner of a domestic dog may prefer to allow the domestic dog access to an area the owner wishes to remain free of dog excrement. For example, a homeowner may prefer a dog to remain in the owner's home while also desiring the home to remain free from dog excreta. To further this desire, a wrap-around canine utility harness used in concert with an integral dog diaper able to contain dog excrement may be of specific interest to the owner. Dogs may prefer not to wear an external garment specifically around a backside area. Domestic pet owners may have difficulty securing and keeping in place a simple pet diaper.

Previous attempts at holding a pet diaper in place have found limited success. These attempts may include a dog diaper fitted with straps or buckles intended to encircle the shoulders of a dog. However, without fully wrapping the trunk of the dog, these attempts may find limited ability to maintain position on the dog.

Therefore, an owner of a domestic dog may find useful an integrated harness diaper apparatus capable of comfortable excrement security on a dog while providing additional utility for control of the dog.

SUMMARY

The present invention may be directed to a wrap-around canine utility harness with integral diaper apparatus configured for capturing excrement and canine control, the apparatus comprising: a longitudinal wrap, the longitudinal wrap further comprising: a dorsal longitudinal section having a cranial end and a caudal end, comprising a pliable fabric configured to cover an area of a dog beginning at a withers area extending caudally along the dorsal to a dorsal rump area and having a dorsal wrap attachment coupled to a caudal-cranial midpoint of the dorsal longitudinal section and a longitudinal attachment clip coupled to a cranial end of the dorsal longitudinal section, the dorsal longitudinal section configured with a dorsal diaper attachment coupled to the caudal end, a tail longitudinal section having a dorsal end and a ventral end, the dorsal end coupled to the caudal end of the dorsal longitudinal section, the tail longitudinal section comprising the pliable fabric configured to cover an area of the dog beginning at the dorsal rump area and extending around a rump area between hind legs to a lower ventral abdomen area of the dog, the tail longitudinal section capable of a longitudinal elastic elongation of a factor of at least approximately one point four (1.4), the tail longitudinal section further comprised of a left section and a right section, the left section and the right section planarly coupled to the caudal end of the dorsal longitudinal section, the left section and the right section vertically coupled to each other at a ventral end of the tail longitudinal section such that a left side of the left section is aligned with a left side of the right section, the left and right sections configured to create a tail opening and surround a base of a tail of the dog as the longitudinal wrap is mounted on the dog; a ventral longitudinal section having a caudal end and a cranial end, comprising the pliable fabric, the ventral longitudinal section configured to cover an area of the dog beginning at the lower ventral abdomen area of the dog and extending cranially to an upper chest area of the dog, the ventral longitudinal section coupled to the ventral end of the tail longitudinal section, the ventral longitudinal section further having an adjustable longitudinal attachment suspender coupled to the cranial end of the ventral longitudinal section and configured to detachably attach to the longitudinal attachment clip, the ventral longitudinal section further configured with a ventral diaper attachment coupled to the caudal end, a trunk wrap perpendicularly joined to the ventral longitudinal section of the longitudinal wrap, the trunk wrap comprising the pliable fabric and configured to encircle a trunk of the dog, the trunk wrap further configured with trunk diaper attachments coupled to a ventral area of the trunk wrap, trunk wrap attachment fasteners coupled to the trunk wrap and configured to detachably attach the trunk wrap to the dorsal wrap attachment as the wrap around canine utility harness is mounted on the dog, a trunk overlap fastener to detachably attach an inner wrap end to an outer wrap end when mounted, an integral diaper garment configured to detachably attach to the wrap around canine utility harness at the dorsal diaper attachment, the ventral diaper attachment, and the trunk diaper attachments, the integral diaper garment comprising: a ventral end, the ventral end configured to be positioned in proximity to a ventral sternum area of the dog as the layered garment is mounted on the wrap around canine utility harness, a dorsal end opposite the ventral end, the dorsal end configured to be positioned in proximity to the dorsal rump area of the dog as the layered garment is mounted on wrap around canine utility harness, a length from dorsal end to ventral end configured to cover an area of the dog: beginning on the ventral sternum area, extending caudally covering the ventral lower abdomen area, wrapping between hind legs and around the rump area, extending cranially from the rump covering a dorsal area, ending on the dorsal back area, a first width equal at the ventral end and at the dorsal end, a second width at a midpoint between the ventral end and the dorsal end, the second width being at most half of the first width, an exterior pliable layer having an interior surface and an exterior surface, the exterior pliable layer further having a shape corresponding to the length, the first width, and the second width of the integral diaper garment, an interior liner coupled to the interior surface of the exterior pliable layer, the interior liner having a shape corresponding to the length, the first width, and the second width of the layered garment, an elongated tail opening co-aligned in the exterior pliable layer and the interior liner, the elongated tail opening positioned and configured with an elastic material to substantially encircle a tail of the dog, an absorbent pad coupled to an interior surface of the interior liner, the absorbent pad of lesser dimension then the interior liner, the absorbent pad having a length able to cover an area: beginning at the ventral end of the interior liner, extending caudally covering the ventral lower abdomen area, ending at the elongated tail opening, the absorbent pad having a width lesser than that of the second width of the integral diaper garment, a dorsal attachment fastener coupled to the exterior surface of the exterior pliable layer, the dorsal attachment fastener configured to couple to the dorsal diaper attachment of the wrap around canine utility harness, a ventral attachment fastener coupled to the exterior surface of the exterior pliable layer, the ventral attachment fastener configured to couple to the ventral diaper attachment of the wrap around canine utility harness, trunk attachment fasteners coupled to the exterior surface of the exterior pliable layer, the trunk attachment fasteners configured to couple to the trunk diaper attachments of the wrap around canine utility harness, wherein the exterior pliable layer, interior liner, absorbent pad, and fasteners are configured to mount to the wrap around canine utility harness and contain an excrement of the dog.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings. It is to be noted the following description and drawings may reference a preferred embodiment of the present invention configured for a dog. While a dog may be one animal for which the invention may be configured, it is to be considered the present invention may be configured for a variety of animals.

A wrap-around canine utility harness with integral diaper apparatus in accordance with of the instant invention may securely maintain the integral diaper in place and thus contain domestic dog excrement.

An owner of a specific domestic dog may find such harness/diaper combination useful. For example, an owner of a puppy yet to be house trained may use the pet harness/diaper until the puppy is trained. Additionally, an owner of an aging or incontinent pet may use the harness to contain dog excrement. Further, an owner of an intact female domestic dog may use the pet harness/diaper during an estrus cycle to contain female discharge and deter unintended pregnancy. Still further, an owner of a domestic dog may use the pet harness/diaper during travel for convenience.

Figure 1:
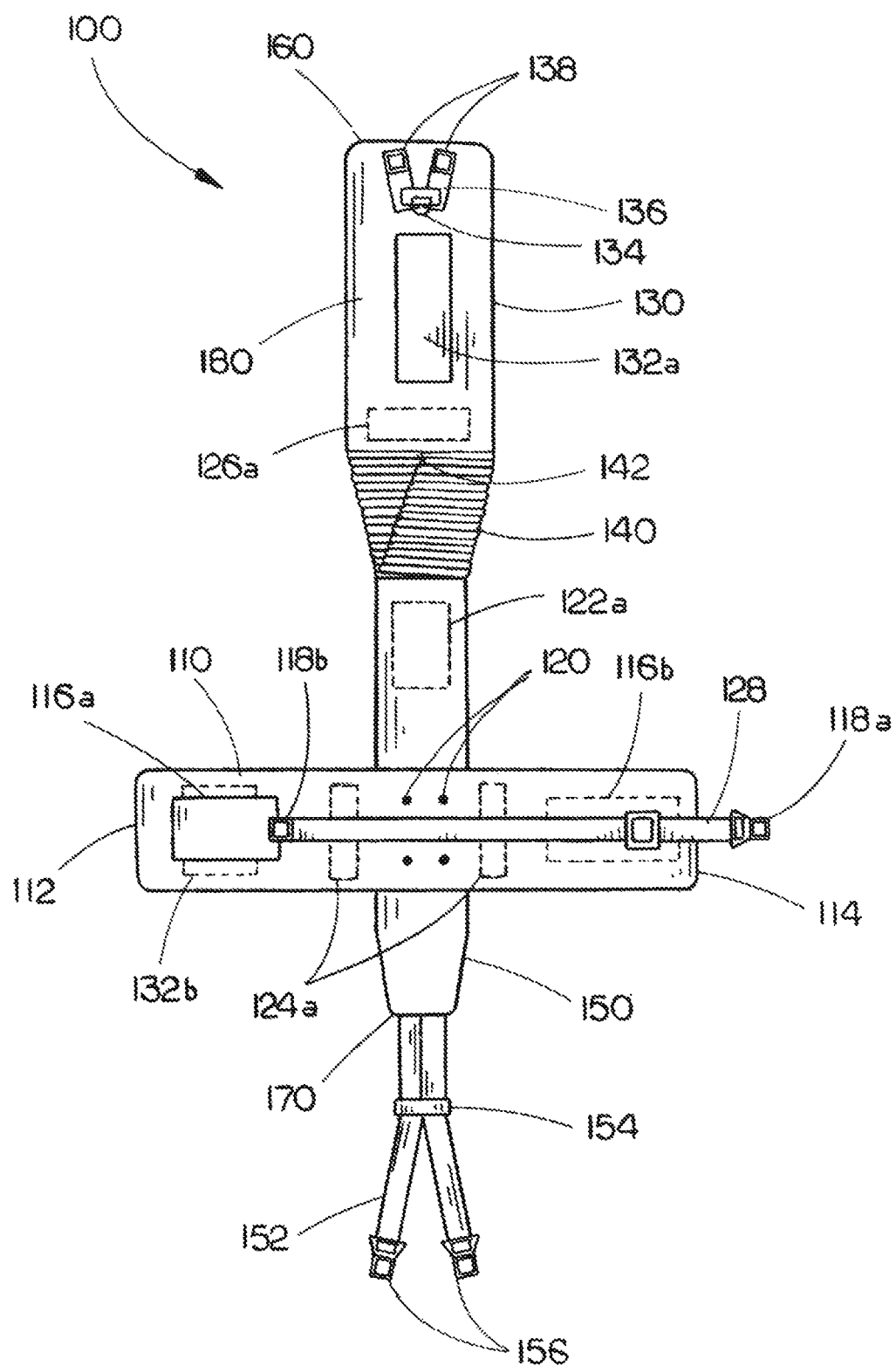
FIG. 1 is an overview of an external side of the harness section in a preferred embodiment of the present invention.

Referring to FIG. 1, an overview of an external side of an apparatus according to a preferred embodiment of the present invention is shown. Wrap-around canine utility harness with integral diaper may comprise a harness section and a diaper section. The harness section may be generally defined as the section providing apparatus support to mount on the dog while supporting the diaper section in place. The diaper section may be generally defined as the section of the apparatus enclosing the anus and urethra areas of both a male and a female dog and absorbing and containing dog excrement.

Harness Section

Figure 2:
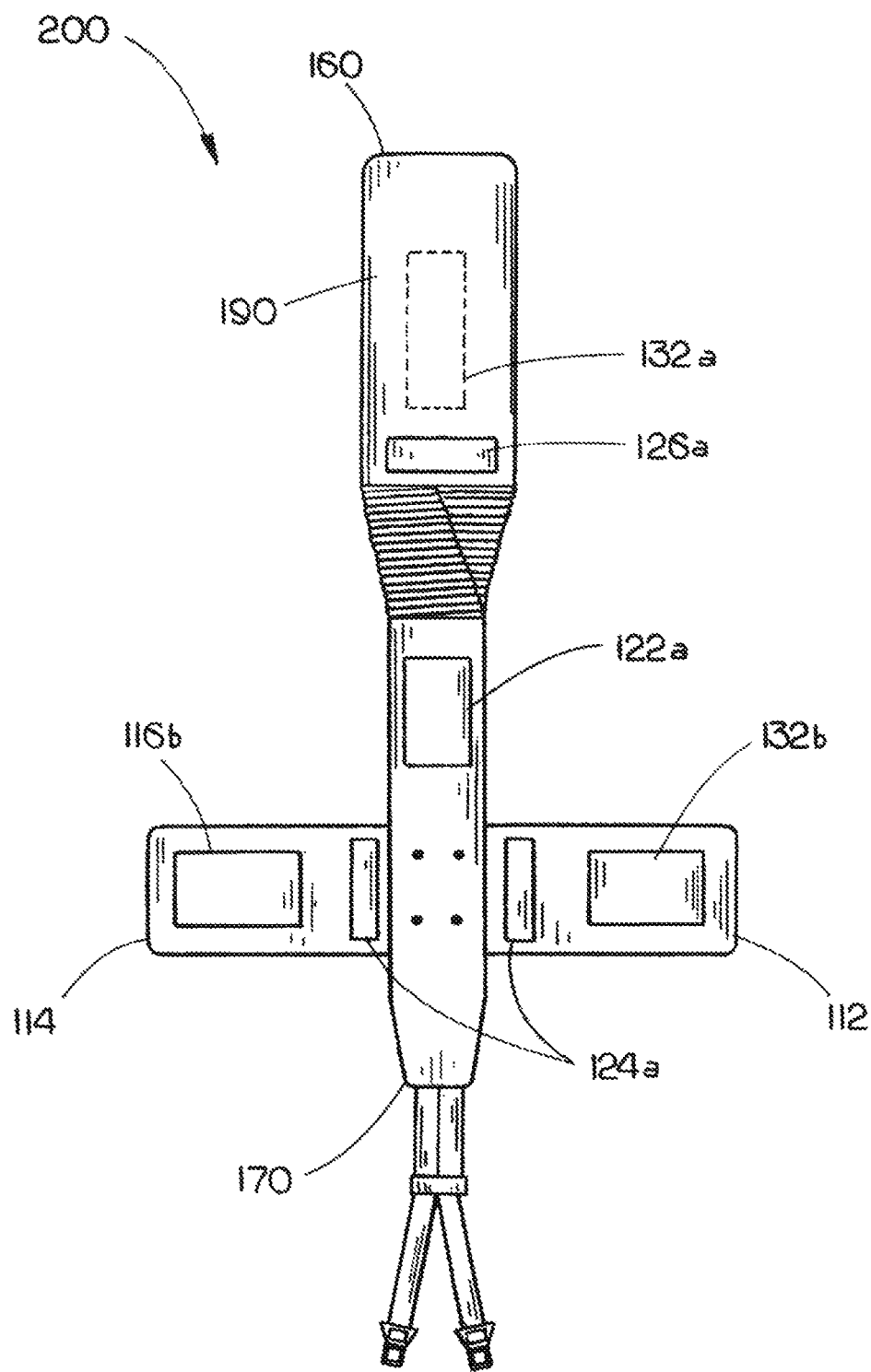
FIG. 2 is an overview of an internal side of the harness section in a preferred embodiment of the present invention.

Referring generally to FIGS. 1 and 2, the harness section may comprise an external side 180 and an internal side 190. The external side 180 may be generally defined as the surface of the harness that, when mounted, is distal from the dog while the internal side 190 may be generally defined as the surface of the apparatus which, when mounted on the dog, is in proximity with the dog.

Construction of the harness section may comprise a first material on the external side 180 and a second material on the internal side. The first material may be of pre-shrunk cotton or other durable pliable fabric able to withstand multiple washings and rigorous dog activity. The second material on the internal side 190 may be comprised of a flannel rubber waterproof sheeting or additional pliable leak-proof material.

Continuing with reference to FIGS. 1 and 2, harness section may further comprise a three-section longitudinal wrap 130, 140, 150. The three coupled sections may comprise a dorsal longitudinal section 130, a tail longitudinal section 140, and a ventral longitudinal section 150. The three coupled sections may form the entirety of the longitudinal wrap 130, 140, 150. The longitudinal wrap may have a dorsal cranial end 160 and a ventral cranial end 170.

The dorsal longitudinal section 130 may maintain a longitudinal dimension of between 6 and 22 inches and a lateral dimension of between 3.5 and 10 inches. For purposes of nomenclature, the longitudinal dimension extends from dorsal cranial end 160 to ventral cranial end 170 and the lateral dimension extends from trunk wrap (described further below) outer wrap end 114 to inner wrap end 112. The dorsal longitudinal section 130 may begin at the dorsal cranial end 160 near a withers area of the dog. The dorsal longitudinal section 130 may continue caudally along the back of the dog ending at a caudal end near the rump of the dog. The dorsal longitudinal section may comprise longitudinal attachment clips 138 configured to detachably couple to adjustable longitudinal attachment suspenders 152 (below) and enable an owner to mount the longitudinal wrap 130, 140, 150 on the dog. D-ring 134 may be coupled to the dorsal longitudinal section allowing an owner to control a dog using the wrap-around canine utility harness as a control device. It is contemplated the strength of the D-ring 134 and the strength of its associated coupling including additional strengthening layers of material 136 may enable a dog owner to lift the weight of the dog by the D-ring 134. A dorsal wrap attachment 132*a* may be coupled to the external side 180 of the dorsal longitudinal section 130. Preferably, dorsal wrap attachment may be of hook and loop design and configured to accept and removable couple to a material of the opposite hook or loop design.

Continuing with reference to FIGS. 1 and 2, the dorsal longitudinal section 130 may further comprise a dorsal diaper attachment 126a. It is contemplated in a preferred embodiment an owner may attach a canine diaper to the wrap-around canine utility harness. The dorsal diaper attachment 126a may be configured to detachably secure the canine diaper to the dorsal longitudinal section 130.

The tail longitudinal section 140 may maintain a dorsal end and a ventral end. The dorsal end of the tail longitudinal section 140 may couple to the caudal end of the dorsal longitudinal section 130. The tail longitudinal section 140 may consist of two individual and equal left and right sections. The left and right sections may be planarly and separately coupled at the dorsal end of the tail longitudinal section 140 to the caudal end of the dorsal longitudinal section 130. The planarly coupling at the dorsal end of the tail longitudinal section 140 may be configured such that a right side of the left section is in proximity to a left side of the right section. The coupling may be configured leaving a tail opening 142 between the left and right sections. The tail opening 142 of sufficient size to allow a tail of the dog to extend through the tail opening 142 as the left and right sections of the tail longitudinal section enclose around a base of the tail as the harness apparatus is mounted on the dog. As the left and right section extend in a caudal direction from the dorsal end, they may preferably begin to overlap to a point where each ventral end of each section is vertically aligned and coupled so a left side of the left section is in proximity to a left side of the right section. As they are coupled together, the left and right sections form the ventral end of the tail longitudinal section 140. The left and right sections may be comprised of an outer layer comprised of the pliable fabric, and an inner elastic structure capable of an elastic elongation and a return to its original shape. The tail longitudinal section may maintain a longitudinal dimension of between 5 and 9 inches. The tail longitudinal section may be further configured for elongation to an extended dimension by a factor of approximately at least 1.4. For example, a 9 inch tail longitudinal section may elastically extend to 13 inches without plastic deformation. The structure and design of tail opening 142 may be of caudal-cranial elongation form to allow caudal-cranial adjustment of longitudinal wrap 130, 140, 150 to securely fit the dog.

Continuing with reference to FIGS. 1 and 2, the ventral longitudinal section 150 may have a caudal end and a cranial end 170. As mounted on the dog, the caudal end may be in proximity with a lower abdomen of the dog while the cranial end may be in proximity with an upper chest area near the sternum of the dog. The ventral longitudinal section may have a longitudinal dimension of between 8 and 26 inches and a lateral dimension of between 2 and 4 inches. The ventral longitudinal section may be configured with joining attachment points 120 to couple the ventral longitudinal section to the trunk wrap 110.

At its caudal end, the ventral longitudinal section 150 may couple to the ventral end of the tail longitudinal section 140. At its cranial end, the ventral longitudinal section may couple to a pair of adjustable longitudinal attachment suspenders 152. The adjustable longitudinal attachment suspenders 152 may extend from the cranial end of the ventral longitudinal section and encircle the neck of the dog and attach to the longitudinal attachment clips 138 using suspender buckles 156. It is contemplated the adjustable longitudinal attachment suspenders 152 may be constructed of elastic material maintaining a resting length of between 3 and 30 inches and a width of between 1 and 3 inches. Adjustable buckle 154 may provide support for the adjustable longitudinal attachment suspenders 152 and additional adjustment to keep the harness apparatus in place around the neck of the dog.

The ventral longitudinal section 150 may further comprise a ventral diaper attachment 122a. It is contemplated in a preferred embodiment an owner may attach a canine diaper to the wrap-around canine utility harness. The ventral diaper attachment 122a may be configured to detachably secure the canine diaper to the ventral longitudinal section 150.

Continuing with reference to FIGS. 1 and 2, wrap-around canine utility harness may further comprise a trunk wrap 110. Preferably, when mounted on a dog, trunk wrap 110 may encircle the trunk of the dog forming a ring around the longitudinal axes of the dog. Trunk wrap 110 may have a inner wrap end 112 and an outer wrap end 114. Trunk wrap 110 may tightly encircle the trunk of the dog, securing the pet diaper harness to the dog. The trunk wrap 110 may be constructed of the pliable fabric and be of a inelastic design. In an alternate embodiment, a portion of the total construction of trunk wrap 110 may be configured with an internal elastic structure enabling the trunk wrap 110 to elastically elongate by approximately four inches. For example, a trunk wrap 110 of a resting 18 inches may elastically elongate to 22 inches as it is tightened and mounted on a dog.

Trunk wrap 110 may further include trunk overlap fasteners 116a and 116b coupled to the trunk wrap 110 to secure the trunk wrap around the dog. Trunk wrap attachment fasteners 116a and 116b may meet as inner wrap end 112 is overlapped by outer wrap end 114. As inner and outer ends 112 and 114 overlap to detachably attach, preferably hook and loop fasteners may be used to join ends 112 and 114. In addition, trunk wrap attachment fastener 132b may detachably attach to dorsal wrap attachment 132a to secure the trunk wrap 110 to the longitudinal wrap 130, 140, 150 on the dorsal of the dog. Preferably, trunk wrap 110 may be configured with an attached adjustable belt strap 128 to provide additional strength to the wrap-around design. Belt strap 128 may be of elastic material, adjustable in length, and configured with belt buckles 118a and 118b to securely connect once the trunk wrap 110 is in place mounted around the trunk of the dog.

Joining attachment points 120 may permanently join trunk wrap 110 to ventral longitudinal section 150 using permanent attachment methods. It is further contemplated joining attachment points 120 may be adjustable allowing an owner to more securely fit and adjustably mount the utility harness to a dog. It is further contemplated joining attachment points 120 may be temporary allowing an owner to detach the trunk wrap 110 from the ventral longitudinal section 150.

The trunk wrap 110 may further comprise a trunk diaper attachment 124a. It is contemplated in a preferred embodiment an owner may attach a canine diaper to the wrap-around canine utility harness. The trunk diaper attachment 124a may be configured to detachably secure the canine diaper to the trunk wrap 110.

It is contemplated the wrap-around canine utility harness apparatus may be constructed in a plurality of sizes. Sizes X-small, Small, Medium, Large, and X-large have been identified in practice as operationally viable. It is contemplated minor adjustments in size may be necessary while still falling within the scope of the present invention. Construction of pet diaper harness apparatus may be in conformance with the following dimensions. All lengths are in US inches:

1. Suspender buckles/Longitudinal attachment clip, 138, 156, Belt buckle 118a & b:
   X small ⅝ inch Small ⅝ inch
Medium ¾ inch
Large 1 inch
X large 1 inch
2. Adjustable Buckle, 154:
X small ⅝ inch
Small ⅝ inch
Medium ¾ inch
Large 1 inch
X large 1 inch
3. D-Ring, 134:
X Small ⅝ inch
Small ⅝ inch
Medium ¾ inch
Large ¾ inch
X Large 1 inch
4. Hook and loop attachment points, 132a & b, 116a & b, (length by width):
X small 3.5×2
Small 6×2
Medium 7×2
Large 8×2
X large 9×3
5. Dorsal longitudinal section, 130 (length by width in inches):
X small 6×3.5
Small 11×5
Medium 14×6
Large 18×8.5
X Large 22×10
6. Tail longitudinal section, 140 (length):
X small 5 inches relaxed-9 inches extended.
Small 6 inches relaxed-10 inches extended.
Medium 7 inches relaxed-11 inches extended.
Large 8 inches relaxed-12 inches extended.
X large 9 inches relaxed-13 inches extended.
7. Ventral longitudinal section 150 (length by width):
X-small 8×2
Small 11×2.5
Medium 14×3
Large 17×3.5
X large 26×4
8. Trunk Wrap, 110 (length by width):
X-small 18×3.5 relaxed-22×3.5 extended
Small 24×5 relaxed-28×5 extended
Medium 30×6 relaxed-34×6 extended
Large 35×8.5 relaxed-39×8.5 extended
X large 40×10 relaxed-44×10 extended
9. Belt Strap 128 (length by width):
X-small 16×⅝
Small 18×⅝
Medium 22×¾
Large 28×1
X large 34×1
10. Suspenders 152 (length by width—each):
X-small 12×⅝
Small 14×⅝
Medium 18×¾
Large 24×1
X large 30×1

Figure 3:
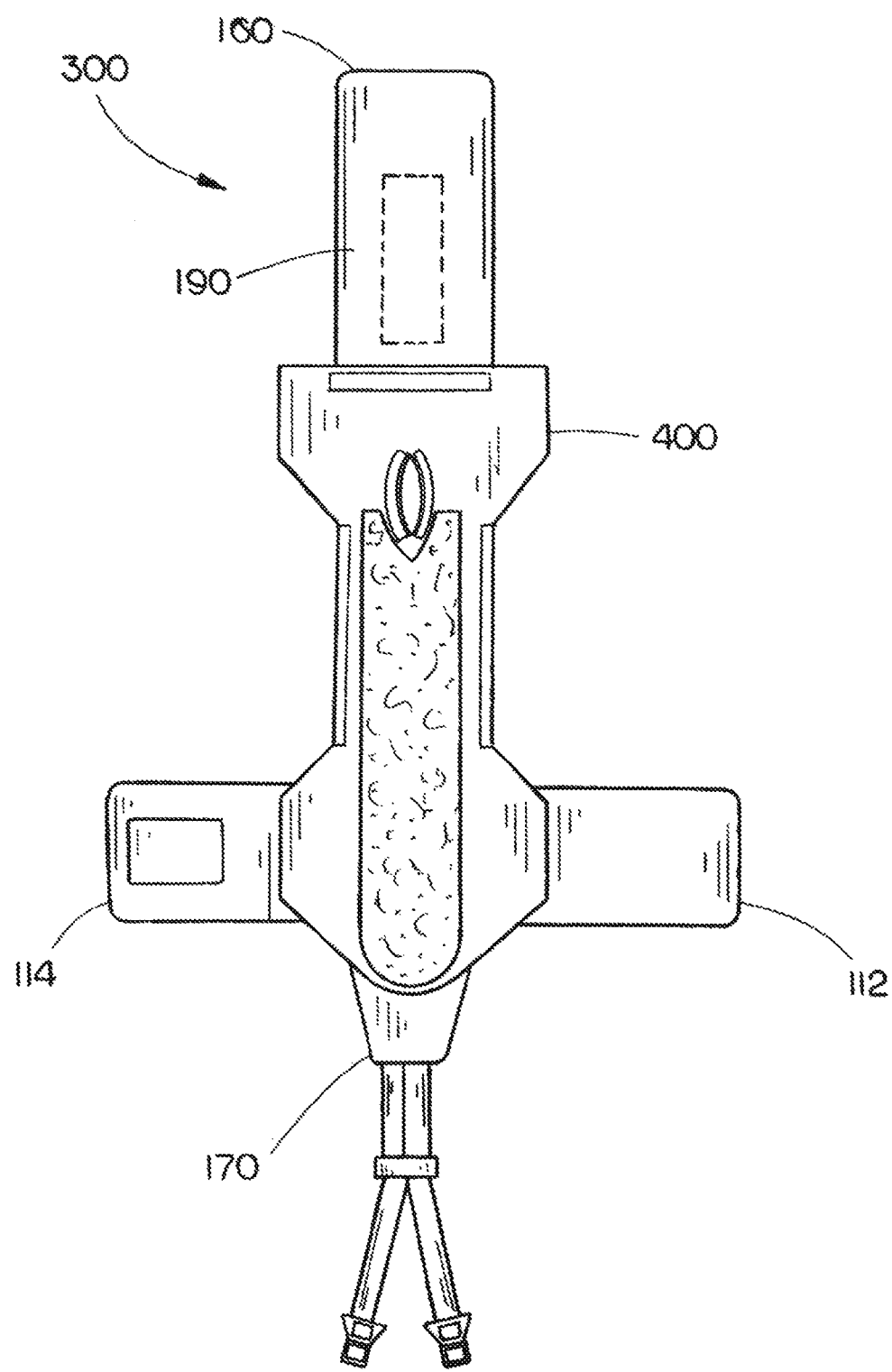
FIG. 3 is an overview of an internal side of the wrap-around canine utility harness with diaper section mounted in a preferred embodiment of the present invention.

Referring to FIG. 3, an overview of an internal side of the harness section with diaper section mounted in a preferred embodiment of the present invention is shown. Integral diaper garment 400 is shown coupled to internal side 190 of wrap-around canine utility harness 100.

Figure 6:
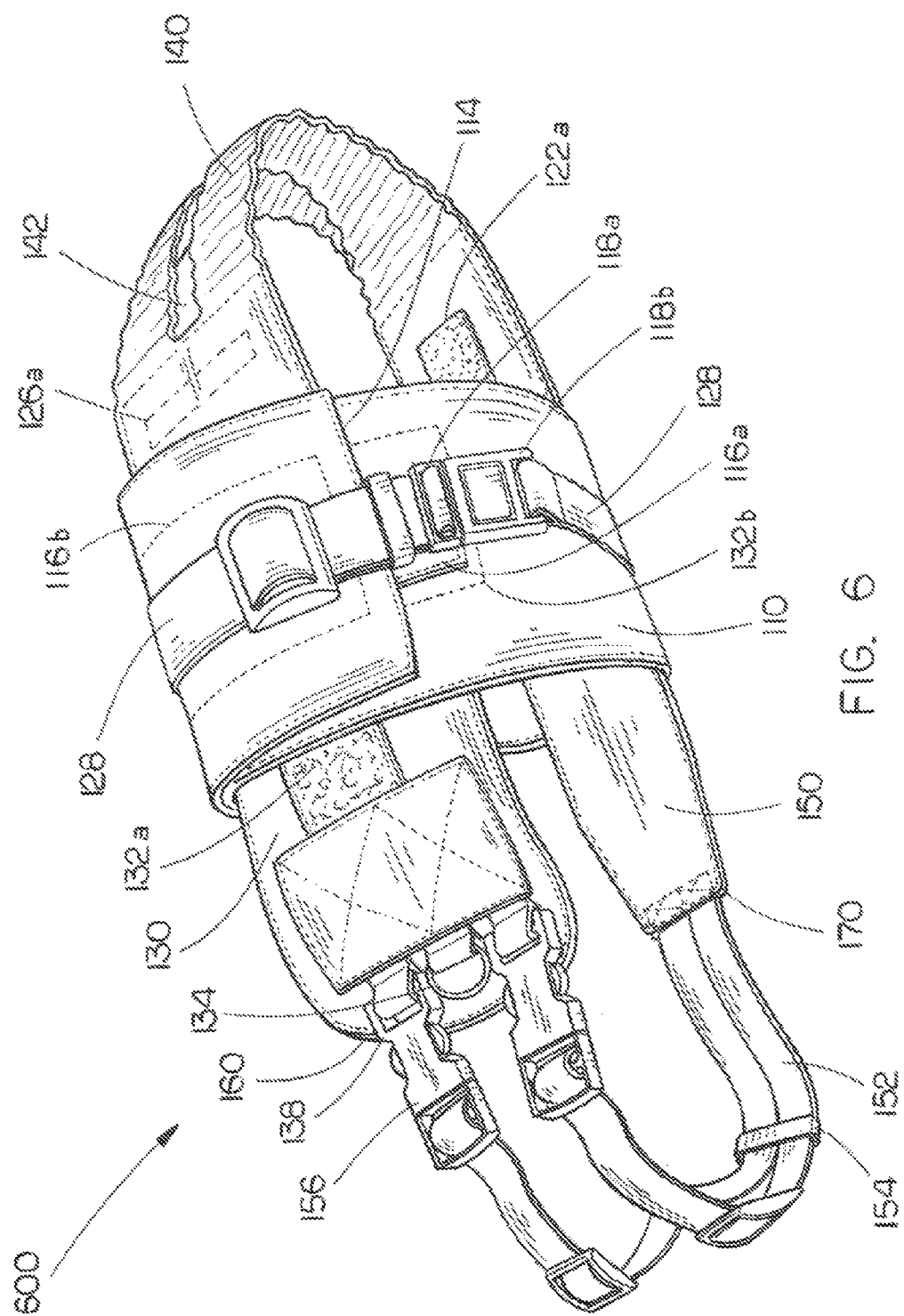
FIG. 6 is a perspective view of an assembled wrap-around canine utility harness of a preferred embodiment of the present invention.

Referring to FIG. 6, a perspective view of an assembled harness section of a preferred embodiment of the present invention is shown. Dorsal 130, tail 140 and ventral 150 sections of the longitudinal wrap are shown with suspenders 152 connected to attachment clips 138. Inner end 112 of trunk wrap 110 is hidden by outer end 114 as dorsal wrap attachment 132a couples with trunk wrap attachment fastener 132b. Of specific interest, left and right tail sections may be seen planarly coupled near the tail opening 142 yet vertically coupled as they join the ventral section 150. The ventral diaper attachment 122a may be seen ready for mounting to the integral diaper garment 400.

Diaper Section

Figure 4:
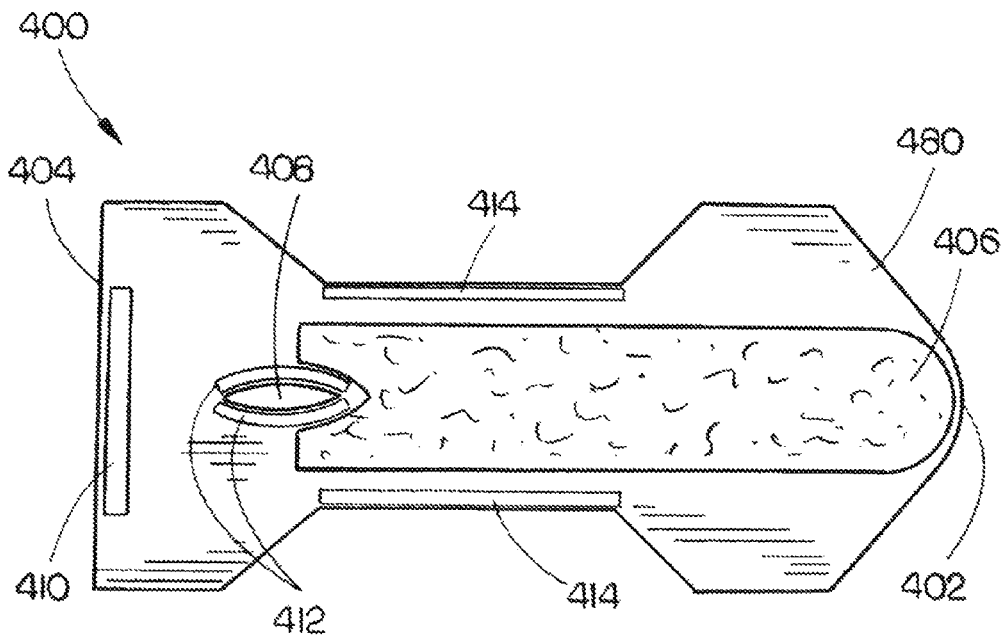
FIG. 4 is a view of an interior side of the integral diaper garment in a preferred embodiment of the present invention.
Figure 5:
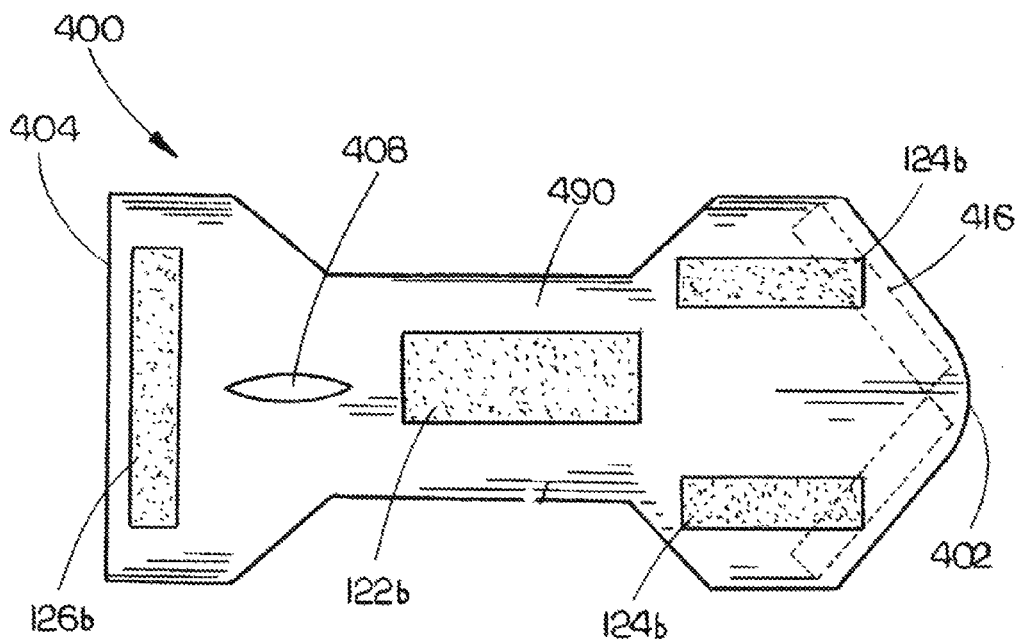
FIG. 5 is a view of an exterior side of the integral diaper garment in a preferred embodiment of the present invention.

Referring to FIGS. 4-5, a view of a preferred embodiment of an integral diaper garment in accordance with the present invention is shown. Embodiments of integral diaper garment 400 may comprise a garment comprising a plurality of layers designed to contain dog excrement.

Layered garment pet diaper 400 may have an interior liner 480 and an exterior pliable layer 490. The interior surface of each layer of the integral diaper garment 400 may be defined as that side of the garment a majority of which is in proximity with the dog while the garment is mounted on the dog. Conversely, the exterior surface of integral diaper garment 400 may be defined as the surface a majority of which is more distant from the dog as the garment is mounted on the dog. Additionally, integral diaper garment may have a dorsal end 404 and a ventral end 402. Dorsal end 404 may be defined as the portion of the garment in proximity with the dorsal or back of the dog while the ventral end 402 may be in proximity with the ventral or belly of the dog.

The exterior pliable layer 490 may be constructed of durable yet breathable material capable of liquid and solid containment while able to withstand rigorous dog use without losing structural integrity. Interior liner 480 may comprise a barrier material suitable for liquid and solid excrement containment. Interior liner 480 may be of similar shape as the exterior pliable layer.

One goal of the integral diaper garment may include maintaining a tight fit around the hind legs and posterior of the dog. Once exterior pliable layer 490 and interior liner 480 are coupled, the result of the coupling may be defined as a shell. Coupled to, and integrally incorporated with the shell may be elastic strips able to return to an initial state after elongated deformation. Leg elastic strips 414, tail elastic strips 412 and dorsal elastic strip 410 may be coupled to the shell where the shell material is compressed or bunched. This compression may create an increased surface area of shell material surrounding the elastic strip as the elastic strip at rest is joined. After joining the elastic strip at rest to compressed or bunched shell, as shell material and elastic strips 410, 412, and 414 may be elongated to a stretched state, shell material may decompress to an original flattened state while elastic strip is stretched. Once shell-elastic combination is released, elastic strip may return to an original resting state causing shell material to return to a compressed state.

To achieve a fitted garment mounted tightly but comfortably against the posterior of the dog, integral diaper garment may include an elongated tail opening 408 constructed generally in a cranial-caudal elongation in exterior pliable layer 490 and aligned with interior liner 480. It is contemplated elongated tail opening 408 may be of alternate lengths to allow pet diaper adjustment in a cranial caudal direction to fit various sizes of dog. Further, elongated tail opening 408 may be of closable construction for a dog having no tail. Additionally, tail elastic strips 412 may be incorporated around elongated tail opening 408 to offer increased closure of elongated tail opening 408 after pet diaper is mounted on the dog. Further, pet diaper may fit tightly against the body of a dog not having a tail as pet diaper does not use the elongated tail opening 408 as a support structure.

Continuing with reference to FIG. 1, to realize the additional goal of containment of dog excrement, integral diaper garment 400 may further comprise absorbent pad 406 coupled to and interior of interior liner 480. Absorbent pad 406 may be of sufficient size to cover an anus and urethra area of the dog yet smaller than an overall interior surface area of the interior liner 480. Specifically, absorbent pad 406 may be configured of sufficient size extending generally from an area aligned and surrounding a midpoint of elongated tail opening 408, extending caudally from the elongated tail opening 408 to cover the dog anus area, wrapping around the dog posterior, extending cranially over the ventral of the dog. The absorbent pad 406 may extend in a cranial direction to a sternum area of the dog and may be of sufficient length and thickness to absorb male dog excreta. Additionally, absorbent pad 406 may be specifically configured to mount on a female dog and contain female specific excreta. Further still, absorbent pad 406 and integral diaper garment 400 may be configured to mount to a female dog and specifically configured to inhibit sexual contact by a male dog.

Preferably, the integral diaper garment 400 may be configured to mount securely to the wrap-around canine utility harness 100. A dorsal attachment fastener 126b may detachably couple with the dorsal diaper attachment 126a. A ventral attachment fastener 122b may detachably couple with the ventral diaper attachment 122a. A trunk attachment fastener 124b may detachably couple with the trunk diaper attachment 124a. It is contemplated the various modes and locations of fastener may be altered to function within the scope of the present invention.

Reinforcements 416 may be integrally constructed between exterior pliable layer 490 and interior liner 480 at ventral end 402. Reinforcements 416 may enable ventral end 402 of pet diaper to fit closely to the ventral portion of the dog as trunk attachment fastener 124b are secured to trunk diaper attachment 124a. Reinforcements 416 embedded within and preferably between exterior pliable layer 490 and interior liner 480 may comprise a pliable material, a rigid material, or a material suitable for additional structural support and the like. In a preferred embodiment, trunk attachment fastener 124b and trunk diaper attachment 124a may comprise a hook and loop design allowing for precise adjustment around the trunk of the dog.

Continuing with reference to FIGS. 4 and 5, Leg elastic strips 414 coupled to exterior pliable layer 490 and interior liner 480 may comprise strips of elastic material. Leg elastic strips 414 serve to enclose a location on pet diaper of anticipated placement around the legs of the dog. It is contemplated leg elastic strips 414 may extend further around the circumference of pet diaper and could extend to meet dorsal elastic strip 410 at the dorsal end 404 of integral diaper garment. Additionally, leg elastic strips 414 may extend toward the ventral end 402 of integral diaper garment and possibly meet the opposite leg elastic strip at the ventral end 402 of pet diaper. Elongated tail opening 408 may be encircled by tail elastic strips 412. Absorbent pad 406 may be coupled to interior liner 480 and may be constructed of well-known materials suitable for liquid absorption and solid waste containment. It is contemplated materials such as superabsorbent polymers, cotton blends, hydrogels, or hydrocolloids and the like may be configured to operate as absorbent pad 406.

The integral diaper garment may be constructed in an hourglass shape having a first width at both the ventral end 402 and opposite dorsal end 404. Near a midpoint between dorsal end 404 and ventral end 402 the shape of integral diaper garment may narrow to a second width. This narrowing may allow for integral diaper garment to securely fit between the hind legs of the dog as the pet diaper is mounted on the dog. Preferably, the second width will be half of the first width. The first width and the second width may be adjustable in integral diaper garment construction to accommodate various sizes of dogs.

As the integral diaper garment is mounted to the wrap-around canine utility harness, the added structure of the wrap-around canine utility harness may increase excrement containment. Added structural strength may be achieved by reinforcements 416 which may allow ventral end 402 to maintain shape around the belly of the dog as the trunk wrap 110 is wrapped around the trunk of the dog and secured in place. Reinforcements 416 may be comprised of curved rigid battens, additional pliable material, extra stitching and the like to reinforce ventral end 402 against deformation as the trunk wrap is pulled to mount wrap-around canine utility harness with integral diaper garment on the dog.

Figure 7:
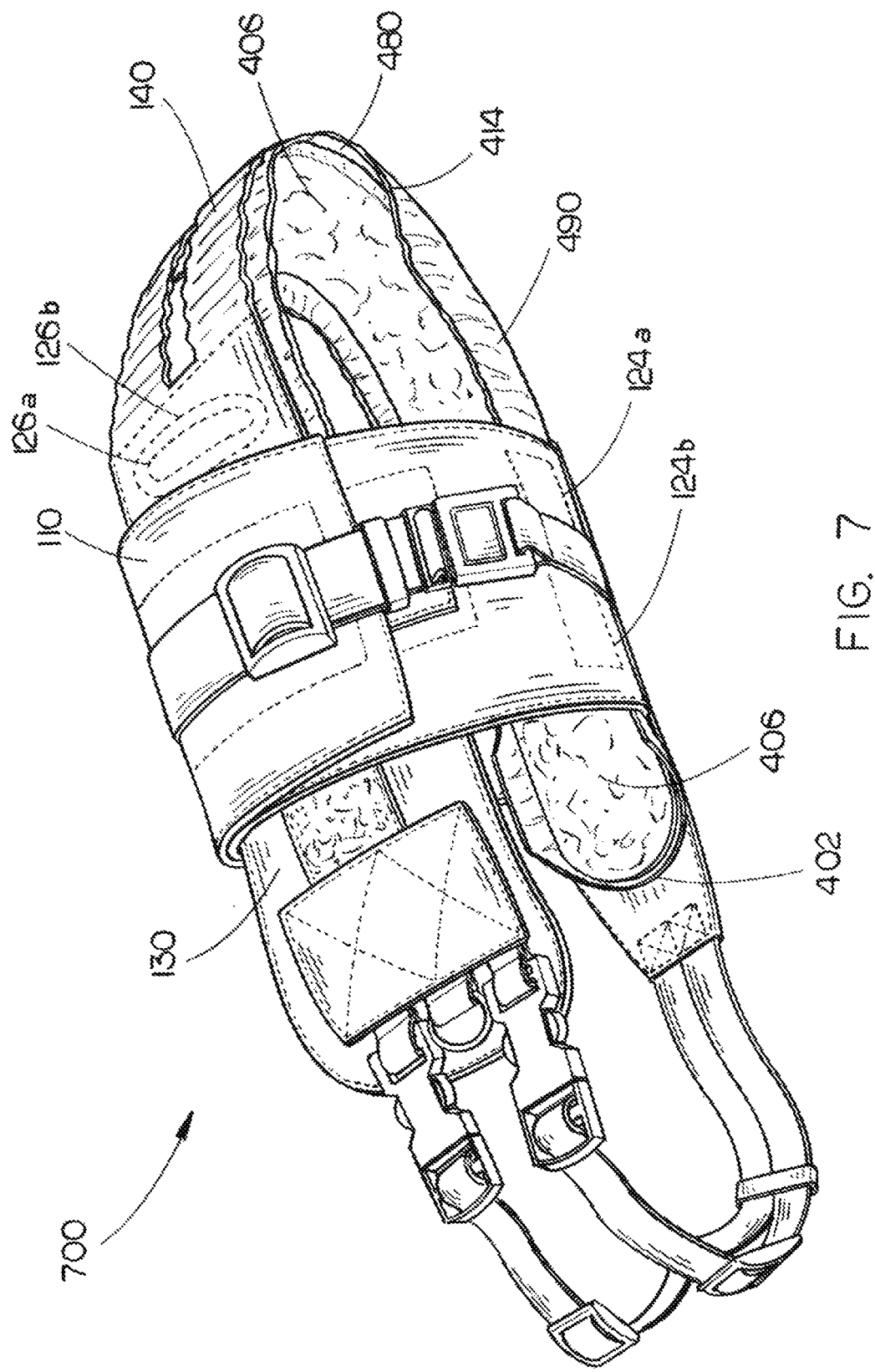
FIG. 7 is a perspective view of an assembled wrap-around canine utility harness with integral diaper garment mounted in a preferred embodiment of the present invention.

Referring to FIG. 7, a perspective view of an assembled wrap-around canine utility harness with integral diaper garment mounted in a preferred embodiment of the present invention is shown. The wrap-around canine utility harness 100 may provide an outer security layer over the top of a majority of the surface area of the integral diaper garment 400. Additionally, outer layer coverage of specific anatomical areas of a dog including the anus and urethra are of primary concern and may be securely covered by the integral diaper garment 400. The ventral attachment fastener 126b may be seen aligning and coupled with ventral diaper attachment 126a. The left trunk attachment fastener 124b may be seen aligning and coupling with trunk diaper attachment 124a. Ventral end 401 of integral diaper garment 400 may be seen extending cranially from the trunk wrap 110. Absorbent pad 406 may be seen covering a majority of the interior liner 480 of the integral diaper garment. Exterior pliable layer 490 may extend to allow leg elastic strips 414 to securely enclose legs of the dog.

Mounting the Wrap on a Dog

For exemplary purposes, a proposed method of mounting the Wrap-around canine utility harness with integral diaper on a dog may include the following steps:
1) lay out the wrap-around canine utility harness on a flat surface with harness external side facing away from the dog;
2) attach the integral diaper to the wrap-around canine utility harness at the dorsal, ventral, and trunk attachment fasteners;
3) place the dog on the surface over the harness/integral diaper with the dog's head corresponding to ventral cranial end 170 of the ventral longitudinal section 150;
4) ensure left and right legs of the dog are straddling either side of the longitudinal wrap, with left legs corresponding to outer wrap end 112 of the trunk wrap 110 and right legs corresponding to inner wrap end 114 of the trunk wrap 110;
5) ensure forward and hind legs of the dog are straddling either side of the trunk wrap 110, with forelegs on the ventral cranial end 170 of ventral longitudinal section 150 and rear legs on the ventral caudal end 160 of dorsal longitudinal section side of the trunk wrap;
6) wrap the wrap-around canine utility harness with integral diaper garment around the dog threading the tail of the dog through the tail openings 142 and 408;

7) connect suspender buckles 156 with clips 138 and adjust adjustable buckle 154 for proper fit;
8) wrap inner wrap end 112 of trunk wrap around the left trunk of the dog, ensuring trunk wrap attachment fastener 132*b* joins with dorsal wrap attachment 132*a*;
9) wrap outer wrap end 114 of trunk wrap 110 around the right trunk of the dog ensuring trunk overlap fastener 116*a* joins to trunk overlap fastener 116*b*;
10) buckle and tighten the belt strap 128 using belt buckles 118*a* and 118*b*.

Figure 8:
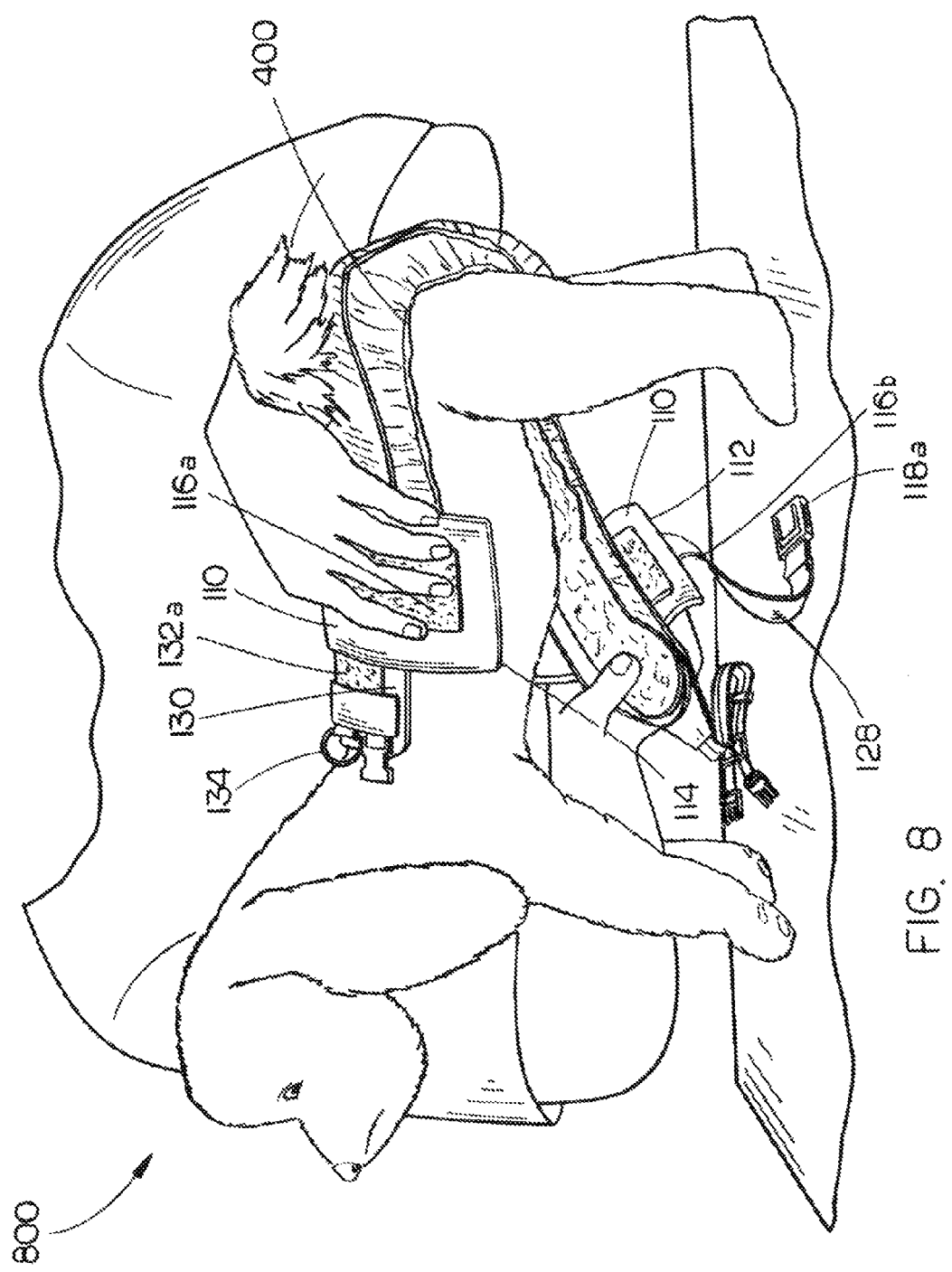
FIG. 8 is a perspective view of an assembled wrap-around canine utility harness with mounted integral diaper garment being mounted on a dog in accordance with a preferred embodiment of the present invention.

Referring to FIG. 8, a lateral view showing the left side of a dog with a preferred embodiment of the present invention being mounted on the dog is shown. In a partial phase of the mounting process longitudinal wrap 130, 140, 150 is shown extending along the dorsal of the dog. Inner wrap end 112 of trunk wrap 110 is in place while outer wrap end 114 is in the process of being attached.

In an additional embodiment of the present invention, wrap-around canine utility harness 100 may be configured to secure, on a dog, a diaper designed for a human. Such human diaper may require alteration before functionality is fully realized when mounted on a dog. It is contemplated an owner of a dog may cut a tail opening in a human diaper to allow the dog tail to remain external to the human diaper.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A wrap-around canine utility harness with integral diaper apparatus configured for capturing excrement and canine control, the apparatus comprising:
   a longitudinal wrap, the longitudinal wrap further comprising:
      a dorsal longitudinal section having a cranial end and a caudal end, comprising a pliable fabric configured to cover an area of a dog beginning at a withers area extending caudally along the dorsal to a dorsal rump area and having a dorsal wrap attachment coupled to a caudal-cranial midpoint of the dorsal longitudinal section and a longitudinal attachment clip coupled to a cranial end of the dorsal longitudinal section, the dorsal longitudinal section configured with a dorsal diaper attachment coupled to said caudal end;
      a tail longitudinal section having a dorsal end and a ventral end, the dorsal end coupled to the caudal end of the dorsal longitudinal section, the tail longitudinal section comprising the pliable fabric configured to cover an area of the dog beginning at the dorsal rump area and extending around a rump area between hind legs to a lower ventral abdomen area of the dog, the tail longitudinal section capable of a longitudinal elastic elongation of a factor of at least approximately one point four (1.4), the tail longitudinal section further comprised of a left section and a right section, said left section and said right section planarly coupled to the caudal end of the dorsal longitudinal section, the left section and the right section vertically coupled to each other at a ventral end of the tail longitudinal section such that a left side of the left section is aligned with a left side of the right section, the left and right sections configured to create a tail opening and surround a base of a tail of the dog as the longitudinal wrap is mounted on the dog;
      a ventral longitudinal section having a caudal end and a cranial end, comprising the pliable fabric, the ventral longitudinal section configured to cover an area of the dog beginning at the lower ventral abdomen area of the dog and extending cranially to an upper chest area of the dog, the ventral longitudinal section coupled to the ventral end of the tail longitudinal section, the ventral longitudinal section further having an adjustable longitudinal attachment suspender coupled to the cranial end of the ventral longitudinal section and configured to detachably attach to the longitudinal attachment clip via a suspender buckle, the ventral longitudinal section further configured with a ventral diaper attachment coupled to said caudal end;
   a trunk wrap perpendicularly joined to the ventral longitudinal section of the longitudinal wrap, the trunk wrap comprising the pliable fabric and configured to encircle a trunk of the dog, the trunk wrap further configured with a trunk diaper attachment coupled to a ventral area of the trunk wrap;
   trunk wrap attachment fasteners coupled to said trunk wrap and configured to detachably attach said trunk wrap to said dorsal wrap attachment as the wrap-around canine utility harness is mounted on the dog;
   a trunk overlap fastener configured to detachably attach an inner wrap end to an outer wrap end when mounted;
   an integral diaper garment configured to detachably attach to the wrap-around canine utility harness at said dorsal diaper attachment, said ventral diaper attachment, and said trunk diaper attachments, the integral diaper garment comprising:
      a ventral end, the ventral end configured to be positioned in proximity to a ventral sternum area of the dog as the layered garment is mounted on the wrap-around canine utility harness;
      a dorsal end opposite said ventral end, the dorsal end configured to be positioned in proximity to the dorsal rump area of the dog as the layered garment is mounted on wrap-around canine utility harness;
      a length from dorsal end to ventral end configured to cover an area of the dog:
         beginning on said ventral sternum area,
         extending caudally covering the ventral lower abdomen area,
         wrapping between hind legs and around the rump area,
         extending cranially from the rump covering a dorsal area,
         ending on said dorsal back area;
      a first width equal at said ventral end and at said dorsal end;
      a second width at a midpoint between said ventral end and said dorsal end, the second width being at most half of said first width;
      an exterior pliable layer having an interior surface and an exterior surface, the exterior pliable layer further having a shape corresponding to the length, the first width, and the second width of said integral diaper garment;
      an interior liner coupled to said interior surface of said exterior pliable layer, the interior liner having a shape corresponding to the length, the first width, and the second width of said layered garment;

an elongated tail opening co-aligned in said exterior pliable layer and said interior liner, said elongated tail opening positioned and configured with an elastic material to substantially encircle a tail of the dog;

an absorbent pad coupled to an interior surface of said interior liner, the absorbent pad of lesser dimension then the interior liner, the absorbent pad having a length able to cover an area:
- beginning at the ventral end of the interior liner;
- extending caudally covering the ventral lower abdomen area;
- ending at the elongated tail opening;

the absorbent pad having a width lesser than that of said second width of said integral diaper garment;

a dorsal attachment fastener coupled to said exterior surface of said exterior pliable layer, the dorsal attachment fastener configured to couple to said dorsal diaper attachment of the wrap-around canine utility harness;

a ventral attachment fastener coupled to said exterior surface of said exterior pliable layer, the ventral attachment fastener configured to couple to said ventral diaper attachment of the wrap-around canine utility harness;

a trunk attachment fastener coupled to said exterior surface of said exterior pliable layer, the trunk attachment fastener configured to couple to said trunk diaper attachment of the wrap-around canine utility harness;

wherein the exterior pliable layer, interior liner, absorbent pad, and fasteners are configured to mount to said wrap-around canine utility harness and contain an excrement of the dog.

2. The apparatus as defined in claim 1, wherein said pliable fabric further comprises an external layer and an internal layer, the external layer a durable preshrunk fabric, the internal layer able to contain a liquid after multiple uses and washings.

3. The apparatus as defined in claim 1, wherein said trunk wrap perpendicularly joined to the ventral longitudinal section of the longitudinal wrap is detachably joined.

4. The apparatus as defined in claim 1, wherein said trunk wrap attachment fasteners, dorsal wrap attachment, and trunk overlap fastener further comprise at least one of hook and loop fasteners, snaps, buttons, hooks, adjustable elastic straps, and magnets.

5. The apparatus as defined in claim 1, wherein said trunk wrap and said longitudinal wrap, when mounted on the dog, are of sufficient strength to maintain position on the dog as the dog is suspended by a D-ring attached to said dorsal longitudinal section of said longitudinal wrap.

6. The apparatus as defined in claim 1, wherein said tail opening is further configured to allow a portion of the tail longitudinal section in proximity to the tail opening to remain in proximity to the dog as the tail of the dog extends through said tail opening.

7. The apparatus as defined in claim 1, wherein said longitudinal wrap is further configured to secure an absorbent garment designed for a human.

8. The apparatus as defined in claim 1, wherein said trunk wrap further comprises an adjustable belt strap external to, and surrounding, said trunk wrap.

9. The adjustable belt strap as in claim 8, wherein said adjustable belt strap comprises elastic material.

10. The apparatus as defined in claim 1, wherein said tail opening is positioned generally in an anticipated tail location on the dog.

11. The apparatus as defined in claim 1, wherein said exterior pliable layer and interior liner further comprise elastic strips coupled to said exterior pliable layer and interior liner, the elastic strips configured within the layered garment to aid in a secure fit of the layered garment around said hind legs and around said posterior of the dog.

12. The apparatus as defined in claim 1, wherein the exterior pliable layer and interior liner further comprise elastic strips coupled to said exterior pliable layer and interior liner, the elastic strips positioned within the layered garment to aid in a secure fit of the layered garment around said elongated tail opening.

13. The apparatus as defined in claim 1, wherein the length from dorsal end to ventral end further comprises a length configured to contain male dog excrement.

14. The apparatus as defined in claim 1, wherein the absorbent pad is further configured with an additional thickness in said ventral sternum area to contain male dog excrement.

15. The apparatus as defined in claim 1, wherein said absorbent pad is specifically sized to mount on a female dog and further configured to inhibit sexual contact by a male dog.

16. The apparatus as defined in claim 1, wherein said width at a midpoint between said ventral end and dorsal end is configured for an unrestricted leg movement of the dog.

* * * * *